United States Patent [19]

Wingert et al.

[11] Patent Number: 5,393,782

[45] Date of Patent: Feb. 28, 1995

[54] THIOAMIDES AND THEIR USE AS CROP PROTECTION AGENTS

[75] Inventors: Horst Wingert; Hubert Sauter; Herbert Bayer, all of Mannheim; Klaus Oberdorf, Heidelberg; Gisela Lorenz, Neustadt; Eberhard Ammermann, Heppenheim, all of Germany

[73] Assignee: BASF Aktiengesellschaft, Ludwigshafen, Germany

[21] Appl. No.: 158,390

[22] Filed: Nov. 29, 1993

[30] Foreign Application Priority Data

Dec. 14, 1992 [DE] Germany .................. 4242081

[51] Int. Cl.6 .................. A01N 37/18; C07C 327/40
[52] U.S. Cl. .................. 514/599; 514/255;
514/269; 514/311; 514/312; 514/345; 514/357;
514/365; 514/372; 544/335; 546/175; 546/290;
546/331; 548/146; 564/74
[58] Field of Search .................. 564/74; 514/599

[56] References Cited

U.S. PATENT DOCUMENTS 5,187,170  2/1993  Wingert et al. .................. 514/357
5,248,687  9/1993  Hayase et al. .................. 514/599

FOREIGN PATENT DOCUMENTS 0398692  11/1990  European Pat. Off. .
0432503  6/1991   European Pat. Off. .
0477631  4/1992   European Pat. Off. .
0528681  2/1993   European Pat. Off. .

Primary Examiner—Shailendra Kumar
Attorney, Agent, or Firm—Oblon, Spivak, McClelland, Maier & Neustadt

[57] ABSTRACT

Thioamides of the formula I

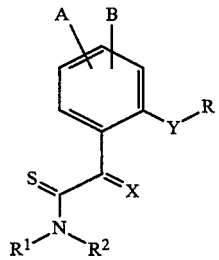

where

A, B, R' are hydrogen, cyano, alkyl, alkoxy or halogen,

X is =CHCH$_3$ or =N—OCH$_3$,

R$^1$, R$^2$ are hydrogen or alkyl,

Y is a group

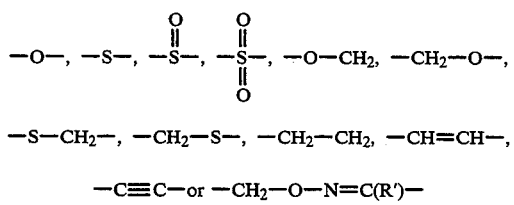

and

R is hydrogen, unsubstituted or substituted alkyl, unsubstituted or substituted cycloalkyl, unsubstituted or substituted aryl or unsubstituted or substituted hetaryl, and pesticides containing these compounds.

7 Claims, No Drawings

THIOAMIDES AND THEIR USE AS CROP PROTECTION AGENTS

The present invention relates to novel thioamides, methods of preparing them, and methods for combating pests, especially fungi, insects, nematodes and mites, with these compounds.

It is known that certain thiocarbamates (EP 432,503) and certain phenylacetamides (cf. EP 477,631 and 398,692) have a fungicidal or insecticidal action. However, their action is unsatisfactory.

We have now surprisingly found that novel thioamides of the formula I

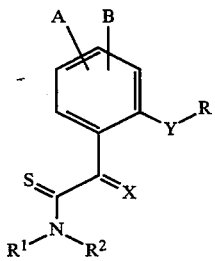

where

A, B, R' are identical or different and each is hydrogen, cyano, $C_1$–$C_4$-alkyl, $C_1$–$C_4$-alkoxy or halogen, X is =CHCH$_3$ or =N—OCH$_3$, R$^1$, R$^2$ are hydrogen or $C_1$–$C_4$-alkyl, Y is a group

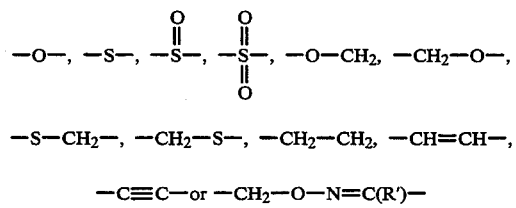

and is hydrogen, unsubstituted or substituted $C_1$–$C_{10}$-alkyl, unsubstituted or substituted $C_1$–$C_6$-cycloalkyl, unsubstituted or substituted aryl or unsubstituted or substituted hetaryl, the term "unsubstituted or substituted" denoting, in addition to hydrogen, halogen, cyano, CO$_2$(-$C_1$–$C_4$-alkyl), C(O) ($C_1$–$C_4$-alkyl), nitro, $C_1$–$C_4$-alkyl, $C_1$–$C_4$-alkoxy, $C_1$–$C_4$-haloalkyl, $C_1$–$C_4$-alkoximino-$C_1$–$C_4$-alkyl, aryl, aryloxy, benzyloxy, hetaryl, hetaryloxy or $C_3$–$C_6$-cycloalkyl and the term "hetaryl" denoting an unsubstituted or substituted aromatic, mono-, di- or trinuclear five-membered or six-membered heterocycle, have an excellent fungicidal, insecticidal, nematicidal and acaricidal action.

The radicals stated in formula I may for example have the following meanings:

A, B, R' may be hydrogen, cyano, $C_1$–$C_4$-alkyl (e.g., methyl), $C_1$–$C_4$-alkoxy (e.g., methoxy) or halogen (fluoro, chloro, bromo, iodo), may be =CHCH$_3$ or =N—OCH$_3$, R$^1$, R$^2$ may be hydrogen or $C_1$–$C_4$-alkyl (e.g., methyl, ethyl)

Y is a group

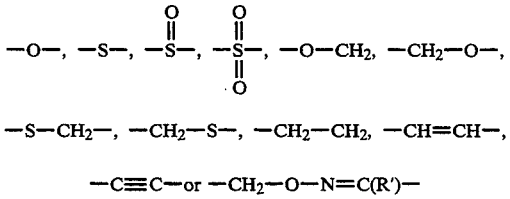

and may be hydrogen, unsubstituted or substituted $C_1$–$C_{10}$-alkyl (e.g., methyl, ethyl, n-, isopropyl, n-, iso-, s-,tert.-butyl, trifluoromethyl, cyanomethyl, benzyl, methoxymethyl), unsubstituted or substituted $C_1$–$C_6$-cycloalkyl (e.g., cyclopropyl, cyclobutyl, cyclopentyl, cyclohexyl, 1-methylcyclopropyl), unsubstituted or substituted aryl (e.g., phenyl, 2-methylphenyl, 3-methoxyphenyl, 4-tert.-butoxyphenyl, naphthyl, 1-methyl-2-naphthyl), unsubstituted or substituted hetaryl (e.g., pyridinyl, 6-Cl-pyridin-2-yl, thiazolyl, 2-benzthiazolyl, furyl, 2-furyl, pyrimidinyl, 4-tDyrimidinyl), the term unsubstituted or substituted" denoting, in addition to hydrogen, halogen (e.g, fluoro, chloro, bromo, iodo), cyano, CO$_2$(-$C_1$–$C_4$-alkyl) (e.g., CO$_2$Me, CO$_2$Et), C(O) ($C_1$–$C_4$-alkyl) (e.g., C(O)CH$_3$), nitro, $C_1$–$C_4$-alkyl (e.g., methyl, ethyl, n-, isopropyl, n-, i-,s-, tert.-butyl), $C_1$–$C_4$-alkoxy (e.g., methoxy, ethoxy, n-, isopropoxy, n-, i-, s-, tert.-butoxy), $C_1$–$C_4$-haloalkyl (e.g., chloromethyl, bromomethyl, trifluoromethyl, 1,1,2,2-tetrafluoroethyl), $C_1$–$C_4$-alkoximino $C_1$–$C_4$-alkyl (e.g., methoximinomethyl, ethoximinomethyl, n-, isopropoximinomethyl, n-, i-, s-, tert.-butoximinomethyl, methoximinoethyl), aryl (e.g., phenyl, 1-, 2-natphthyl), aryloxy (phenoxy, 2-naphthyloxy), benzyloxy, hetaryl (e.g., pyridyl, pyrimidinyl, pyridazinyl, quinolinyl, furyl, thienyl, oxazolyl, isoxazolyl, benzthiazolyl, benzthienyl, benzoxazolyl, pyrryl), hetaryloxy (e.g., 2-pyridinyloxy, 2-quinolinyloxy, 4-pyrimidinyloxy), $C_3$–$C_6$-cycloalkyl (e.g., cyclopropyl, cyclobutyl, cyclopentyl, cyclohexyl) and the term "hetaryl" denoting an unsubstituted or substituted aromatic mono-, di- or trinuclear five-membered or six-membered heterocycle (e.g., pyridine, quinoline, pyrimidine, benzthiazole, benzoxazole).

Preferred compounds of the formula I

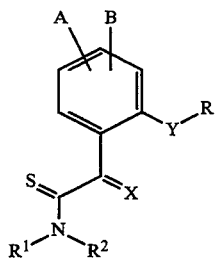

are those in which
A, B, are hydrogen,
X is =N—OMe,
R$^1$ is hydrogen,
R$^2$ is methyl,
and Y, R' and R have the meanings given in claim 1.

The novel compounds of the formula I may, because of the C=C— or C=N— double bonds, be obtained as E/Z isomer mixtures. These may be separated into their individual components in conventional manner, e.g., crystallization or chromatography. Both the individual isomeric compounds and mixtures thereof are encompassed by the invention and can be used as pesticides.

The thioamides of the formula I are prepared for example by reacting amides of the formula II in conventional manner (cf. e.g., Houben-Weyl, vol. IX, pp. 764 et seq.) with a sulfurizing agent such as $P_4S_{10}$ or Lawesson's reagent

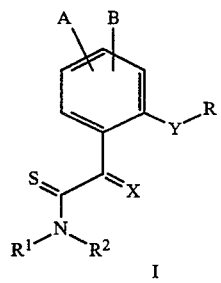

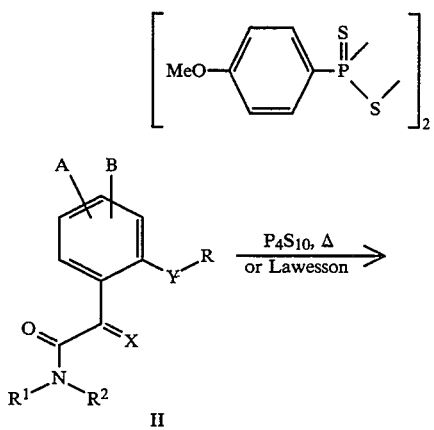

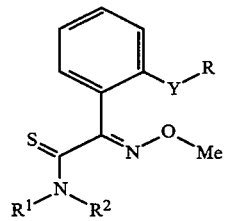

The amides II are known or can be prepared by analogy to known methods (cf. EP 477631, 398692, 463488).

The preparation of the compounds is illustrated by the following examples.

EXAMPLE 1

Preparation of 2-methoximino-2-[2'-(o-methylphenoxymethyl)-phenyl]acetic acid-N-methylthioamide (compound 2, Table 1).

5 g (16 mmol) of 2-methoximino-2-[2'-(o-methylphenoxymethyl)-phenyl]acetic acid-N-methylamide (disclosed in EP 477631) and 8.1 g (20 mmol) of Lawesson's reagent are refluxed for 90 minutes in 50 ml of xylene. The solvent is then removed under reduced pressure. The residue was chromatographed twice on silica gel using mixtures of hexane and methyl tert-butyl ether, and 1.7 g (32%) of the compound was obtained as a yellow oil.

$^1$H-NMR (CDCl$_3$/TMS): δ=2.25 (CH$_3$); 3.21 (d, NHCH$_3$), 3.95 (OCH$_3$); 4.97 (CH$_2$); 6.79–7.55 (aryl, 8H); 8.57 (NH).

The compounds listed in the tables below may be obtained analogously:

TABLE 1

| No. | Y | R$^1$ | R$^2$ | R | Phys. data m. p. [°C.] IR [cm$^{-1}$] H-NMR [ppm] |
|---|---|---|---|---|---|
| 1 | —CH$_2$O— | Me | H | phenyl | |
| 2 | —CH$_2$O— | Me | H | 2-Me-phenyl | 3360, 2940, 1595, 1520, 1494, 1241, 1228, 1122, 1052, 1025, 929, 752 |
| 3 | —CH$_2$O— | Me | H | 3-Me-phenyl | |
| 4 | —CH$_2$O— | Me | H | 4-Me-phenyl | |
| 5 | —CH$_2$O— | Me | H | 2-Cl-phenyl | |
| 6 | —CH$_2$O— | Me | H | 3-Cl-phenyl | |
| 7 | —CH$_2$O— | Me | H | 4-Cl-phenyl | |
| 8 | —CH$_2$O— | Me | H | 2-F-phenyl | |
| 9 | —CH$_2$O— | Me | H | 3-F-phenyl | |
| 10 | —CH$_2$O— | Me | H | 4-F-phenyl | |
| 11 | —CH$_2$O— | Me | H | 2-Br-phenyl | |
| 12 | —CH$_2$O— | Me | H | 3-Br-phenyl | |
| 13 | —CH$_2$O— | Me | H | 4-Br-phenyl | |
| 14 | —CH$_2$O— | Me | H | 2-OCH$_3$-phenyl | |
| 15 | —CH$_2$O— | Me | H | 3-OCH$_3$-phenyl | |
| 16 | —CH$_2$O— | Me | H | 4-OCH$_3$-phenyl | |
| 17 | —CH$_2$O— | Me | H | 2-CF$_3$-phenyl | |
| 18 | —CH$_2$O— | Me | H | 3-CF$_3$-phenyl | |
| 19 | —CH$_2$O— | Me | H | 4-CF$_3$-phenyl | |
| 20 | —CH$_2$O— | Me | H | 2-CO$_2$Me-phenyl | |
| 21 | —CH$_2$O— | Me | H | 3-CO$_2$Me-phenyl | |

TABLE 1-continued

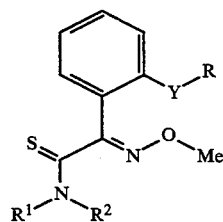

| No. | Y | R¹ | R² | R | Phys. data m. p. [°C.] IR [cm⁻¹] H-NMR [ppm] |
|---|---|---|---|---|---|
| 22 | —CH₂O— | Me | H | 4-CO₂Me-phenyl | |
| 23 | —CH₂O— | Me | H | 2,3-Me₂-phenyl | |
| 24 | —CH₂O— | Me | H | 2,4-Me₂-phenyl | |
| 25 | —CH₂O— | Me | H | 2,5-Me₂-phenyl | 3360, 2935, 1583, 1519, 1509, 1458, 1358, 1262, 1154, 1130, 1026 |
| 26 | —CH₂O— | Me | H | 2,6-Me₂-phenyl | |
| 27 | —CH₂O— | Me | H | 3,4-Me₂-phenyl | |
| 28 | —CH₂O— | Me | H | 3,5-Me₂-phenyl | |
| 29 | —CH₂O— | Me | H | 2,3-Cl₂-phenyl | |
| 30 | —CH₂O— | Me | H | 2,4-Cl₂-phenyl | |
| 31 | —CH₂O— | Me | H | 2,5-Cl₂-phenyl | |
| 32 | —CH₂O— | Me | H | 2,6-Cl₂-phenyl | |
| 33 | —CH₂O— | Me | H | 3,4-Cl₂-phenyl | |
| 34 | —CH₂O— | Me | H | 3,5-Cl₂-phenyl | |
| 35 | —CH₂O— | Me | H | 2-Cl—, 4-Me-phenyl | |
| 36 | —CH₂O— | Me | H | 2-Cl—, 5-Me-phenyl | |
| 37 | —CH₂O— | Me | H | 2-Me—, 4-Cl-phenyl | |
| 38 | —CH₂O— | Me | H | 2-Me—, 5-Cl-phenyl | |
| 39 | —CH₂O— | Me | H | 2-pyridyl | |
| 40 | —CH₂O— | Me | H | 3-pyridyl | |
| 41 | —CH₂O— | Me | H | 4-pyridyl | |
| 42 | —CH₂O— | Me | H | 6-Cl-2-pyridyl | |
| 43 | —CH₂O— | Me | H | 6-OCH₃-2-pyridyl | |
| 44 | —CH₂O— | Me | H | 6-Me-2-pyridyl | |
| 45 | —CH₂O— | Me | H | 5-CF₃-2-pyridyl | |
| 46 | —CH₂O— | Me | H | 2-quinolyl | |
| 47 | —CH₂O— | Me | H | 3-Me-2-quinolyl | |
| 48 | —CH₂O— | Me | H | 8-Me-2-quinolyl | |
| 49 | —CH₂O— | Me | H | 2-pyrimidinyl | |
| 50 | —CH₂O— | Me | H | 4-CF₃-2-pyrimidinyl | |
| 51 | —CH₂O— | Me | H | benzothiazol-2-yl | |
| 52 | —CH₂O— | Me | H | 5-Cl-benzothiazol-2-yl | |
| 53 | —CH₂O— | Me | H | 6-Cl-benzothiazol-2-yl | |
| 54 | —CH₂O— | Me | H | 2-Me-4-methoximinoethyl-1-phenyl | 2.18; 2.27 (CH₃); 3.24 (d, NHCH₃); 3.96; 3.97 (OCH₃); 4.98 (CH₂); 6.79–7.51 (Aryl, 7H); 8.61 ppm (NH). |
| 55 | —CH₂O— | Me | H | 2-Me-5-methoximinomethyl-phenyl | |
| 56 | —CH₂O— | Me | H | 2,5-Me₂-4-methoximinomethyl-phenyl | |
| 57 | —CH₂O— | Me | H | 2-Me-4-ethoximinomethyl-phenyl | |
| 58 | —CH₂O— | Me | H | 2-Me-5-ethoximinomethyl-phenyl | |
| 59 | —CH₂O— | Me | H | 2,5-Me₂-4-ethoximinomethyl-phenyl | |
| 60 | —CH₂O— | Me | H | 2-Me-4-n-butoximinomethyl-phenyl | |
| 61 | —CH₂O— | Me | H | 2,5-Me₂-4-n-butoximinomethyl-phenyl | |
| 62 | —CH₂O— | Me | H | 2-Me-4-allyloximinomethyl-phenyl | |
| 63 | —CH₂O— | Me | H | 2,5-Me₂-4-allyloximinomethyl-phenyl | |
| 64 | —CH₂O— | Me | H | 1-naphthyl | |
| 65 | —CH₂O— | Me | H | 2-naphthyl | |
| 66 | —CH₂O— | Me | H | 1-methyl-2-naphthyl | |
| 67 | —CH₂O— | Me | H | methyl | |
| 68 | —O—CH₂— | Me | H | H | |
| 69 | —O—CH₂— | Me | H | phenyl | |
| 70 | —O—CH₂— | Me | H | 2-Cl-phenyl | |
| 71 | —O—CH₂— | Me | H | 2-Me-phenyl | |
| 72 | —CH₂S— | Me | H | Me | |
| 73 | —CH₂S— | Me | H | phenyl | |
| 74 | —CH₂S— | Me | H | 2-Me-phenyl | |
| 75 | —CH₂S— | Me | H | 2,5-Cl₂-phenyl | |
| 76 | —CH₂S— | Me | H | 2-pyridyl | |
| 77 | —CH₂S— | Me | H | 6-Cl-2-pyridyl | |
| 78 | —CH₂S— | Me | H | benzothiazol-2-yl | |
| 79 | —CH₂S— | Me | H | 5-Cl-benzothiazol-2-yl | |
| 80 | —CH₂S— | Me | H | 6-Cl-benzothiazol-2-yl | |
| 81 | —O— | Me | H | phenyl | |
| 82 | —O— | Me | H | 2-naphthyl | |

TABLE 1-continued

Structure: phenyl ring with ortho Y-R substituent and C(=S)N(R¹)(R²) and C(=NOMe) groups

| No. | Y | R¹ | R² | R | Phys. data m. p. [°C.] IR [cm⁻¹] H-NMR [ppm] |
|-----|---|----|----|---|---|
| 83 | —O— | Me | H | 2-Me-phenyl | |
| 84 | —O— | Me | H | 3-Me-phenyl | |
| 85 | —O— | Me | H | 4-Me-phenyl | |
| 86 | —O— | Me | H | 2-Cl-phenyl | |
| 87 | —O— | Me | H | 3-Cl-phenyl | |
| 88 | —O— | Me | H | 4-Cl-phenyl | |
| 89 | —O— | Me | H | 3-phenoxy-phenyl | |
| 90 | —O— | Me | H | 6-(2-CN-phenoxy)-pyrimidin-4-yl | |
| 91 | —O— | Me | H | 2-pyridyl | |
| 92 | —C≡C— | Me | H | phenyl | |
| 93 | —C≡C— | Me | H | 2-Me-phenyl | |
| 94 | —C≡C— | Me | H | 3-Me-phenyl | |
| 95 | —C≡C— | Me | H | 4-Me-phenyl | |
| 96 | —C≡C— | Me | H | 2-Cl-phenyl | |
| 97 | —C≡C— | Me | H | 2,5-Me₂-phenyl | |
| 98 | —CH₂—O—N=C(Me)— | Me | H | phenyl | |
| 99 | —CH₂—O—N=C(Me)— | Me | H | 2-Me-phenyl | |
| 100 | —CH₂—O—N=C(Me)— | Me | H | 3-Me-phenyl | |
| 101 | —CH₂—O—N=C(Me)— | Me | H | 4-Me-phenyl | |
| 102 | —CH₂—O—N=C(Me)— | Me | H | 2-Cl-phenyl | |
| 103 | —CH₂—O—N=C(Me)— | Me | H | 3-Cl-phenyl | |
| 104 | —CH₂—O—N=C(Me)— | Me | H | 4-Cl-phenyl | |
| 104 | —CH₂—O—N=C(Me)— | Me | H | 2-F-phenyl | |
| 105 | —CH₂—O—N=C(Me)— | Me | H | 3-F-phenyl | |
| 106 | —CH₂—O—N=C(Me)— | Me | H | 4-F-phenyl | |

TABLE 1-continued

| No. | Y | R¹ | R² | R | Phys. data m. p. [°C.] IR [cm⁻¹] H-NMR [ppm] |
|---|---|---|---|---|---|
| 107 | —CH₂—O—N=C(Me) | Me | H | 2-Br-phenyl | |
| 108 | —CH₂—O—N=C(Me) | Me | H | 3-Br-phenyl | |
| 109 | —CH₂—O—N=C(Me) | Me | H | 4-Br-phenyl | |
| 110 | —CH₂—O—N=C(Me) | Me | H | 2-CF₃-phenyl | |
| 111 | —CH₂—O—N=C(Me) | Me | H | 3-CF₃-phenyl | |
| 112 | —CH₂—O—N=C(Me) | Me | H | 4-CF₃-phenyl | |
| 113 | —CH₂—O—N=C(Me) | Me | H | 2-OCH₃-phenyl | |
| 114 | —CH₂—O—N=C(Me) | Me | H | 3-OCH₃-phenyl | |
| 115 | —CH₂—O—N=C(Me) | Me | H | 4-OCH₃-phenyl | |
| 116 | —CH₂—O—N=C(Me) | Me | H | 2-CO₂Me-phenyl | |
| 117 | —CH₂—O—N=C(Me) | Me | H | 3-CO₂Me-phenyl | |
| 118 | —CH₂—O—N=C(Me) | Me | H | 4-CO₂Me-phenyl | |
| 119 | —CH₂—O—N=C(Me) | Me | H | 2,3-Me₂-phenyl | |

TABLE 1-continued

Structure: phenyl ring with substituents Y-R (ortho), and C(=S)-N(R¹)(R²) with =N-O-Me group.

| No. | Y | R¹ | R² | R | Phys. data m. p. [°C.] IR [cm⁻¹] H-NMR [ppm] |
|---|---|---|---|---|---|
| 120 | —CH₂—O—N=C(Me)— | Me | H | 2,4-Me₂-phenyl | |
| 121 | —CH₂—O—N=C(Me)— | Me | H | 2,5-Me₂-phenyl | |
| 122 | —CH₂—O—N=C(Me)— | Me | H | 2,6-Me₂-phenyl | |
| 123 | —CH₂—O—N=C(Me)— | Me | H | 3,4-Me₂-phenyl | |
| 124 | —CH₂—O—N=C(Me)— | Me | H | 3,5-Me₂-phenyl | |
| 125 | —CH₂—O—N=C(Me)— | Me | H | 2,3-Cl₂-phenyl | |
| 126 | —CH₂—O—N=C(Me)— | Me | H | 2,4-Cl₂-phenyl | |
| 127 | —CH₂—O—N=C(Me)— | Me | H | 2,5-Cl₂-phenyl | |
| 128 | —CH₂—O—N=C(Me)— | Me | H | 2,6-Cl₂-phenyl | |
| 129 | —CH₂—O—N=C(Me)— | Me | H | 3,4-Cl₂-phenyl | |
| 130 | —CH₂—O—N=C(Me)— | Me | H | 3,5-Cl₂-phenyl | 3360, 1583, 1556, 1518, 1409, 1358, 1304, 102, 856, 834, 800 cm⁻¹. |
| 131 | —CH₂—O—N=C(Me)— | Me | H | 2-Cl—, 4-Me-phenyl | |
| 132 | —CH₂—O—N=C(Me)— | Me | H | 2-Cl—, 5-Me-phenyl | |

TABLE 1-continued

|  |  |  |  |  |  | Phys. data m. p. [°C.] |
|---|---|---|---|---|---|---|
| No. | Y |  | R¹ | R² | R | IR [cm⁻¹] H-NMR [ppm] |
| 133 | —CH₂—O—N= | Me | Me | H | 2-Me—, 4-Cl-phenyl |  |
| 134 | —CH₂—O—N= | Me | Me | H | 2-Me—, 5-Cl-phenyl |  |
| 135 | —CH₂—O—N= | Me | Me | H | 2-pyridyl |  |
| 136 | —CH₂—O—N= | Me | Me | H | 2-naphthyl |  |
| 137 | —CH₂—O—N= | Me | Me | H | 1-Me-2-naphthyl |  |
| 138 | —CH₂—O—N= | Me | Me | H | 2-furyl |  |
| 139 | —CH₂—O— |  | Me | Me | phenyl |  |
| 140 | —CH₂—O— |  | Et | H | phenyl |  |
| 141 | —CH₂—O— |  | Et | Et | phenyl |  |

TABLE 2

|  |  |  |  |  | Phys. data m. p. [°C.] |
|---|---|---|---|---|---|
| No. | Y | R¹ | R² | R | IR [cm⁻¹] H-NMR [ppm] |
| 1 | —CH₂O— | Me | H | phenyl |  |
| 2 | —CH₂O— | Me | H | 2-Me-phenyl |  |
| 3 | —CH₂O— | Me | H | 3-Me-phenyl |  |
| 4 | —CH₂O— | Me | H | 4-Me-phenyl |  |
| 5 | —CH₂O— | Me | H | 2-Cl-phenyl |  |
| 6 | —CH₂O— | Me | H | 3-Cl-phenyl |  |
| 7 | —CH₂O— | Me | H | 4-Cl-phenyl |  |
| 8 | —CH₂O— | Me | H | 2-F-phenyl |  |
| 9 | —CH₂O— | Me | H | 3-F-phenyl |  |
| 10 | —CH₂O— | Me | H | 4-F-phenyl |  |
| 11 | —CH₂O— | Me | H | 2-Br-phenyl |  |
| 12 | —CH₂O— | Me | H | 3-Br-phenyl |  |
| 13 | —CH₂O— | Me | H | 4-Br-phenyl |  |
| 14 | —CH₂O— | Me | H | 2-OCH₃-phenyl |  |
| 15 | —CH₂O— | Me | H | 3-OCH₃-phenyl |  |
| 16 | —CH₂O— | Me | H | 4-OCH₃-phenyl |  |
| 17 | —CH₂O— | Me | H | 2-CF₃-phenyl |  |

TABLE 2-continued

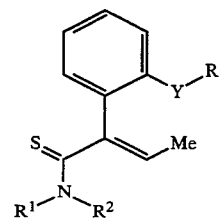

| No. | Y | $R^1$ | $R^2$ | R | Phys. data m. p. [°C.] IR [cm$^{-1}$] H-NMR [ppm] |
|---|---|---|---|---|---|
| 18 | —CH$_2$O— | Me | H | 3-CF$_3$-phenyl | |
| 19 | —CH$_2$O— | Me | H | 4-CF$_3$-phenyl | |
| 20 | —CH$_2$O— | Me | H | 2-CO$_2$Me-phenyl | |
| 21 | —CH$_2$O— | Me | H | 3-CO$_2$Me-phenyl | |
| 22 | —CH$_2$O— | Me | H | 4-CO$_2$Me-phenyl | |
| 23 | —CH$_2$O— | Me | H | 2,3-Me$_2$-phenyl | |
| 24 | —CH$_2$O— | Me | H | 2,4-Me$_2$-phenyl | |
| 25 | —CH$_2$O— | Me | H | 2,5-Me$_2$-phenyl | |
| 26 | —CH$_2$O— | Me | H | 2,6-Me$_2$-phenyl | |
| 27 | —CH$_2$O— | Me | H | 3,4-Me$_2$-phenyl | |
| 28 | —CH$_2$O— | Me | H | 3,5-Me$_2$-phenyl | |
| 29 | —CH$_2$O— | Me | H | 2,3-Cl$_2$-phenyl | |
| 30 | —CH$_2$O— | Me | H | 2,4-Cl$_2$-phenyl | |
| 31 | —CH$_2$O— | Me | H | 2,5-Cl$_2$-phenyl | |
| 32 | —CH$_2$O— | Me | H | 2,6-Cl$_2$-phenyl | |
| 33 | —CH$_2$O— | Me | H | 3,4-Cl$_2$-phenyl | |
| 34 | —CH$_2$O— | Me | H | 3,5-Cl$_2$-phenyl | |
| 35 | —CH$_2$O— | Me | H | 2-Cl—, 4-Me-phenyl | |
| 36 | —CH$_2$O— | Me | H | 2-Cl—, 5-Me-phenyl | |
| 37 | —CH$_2$O— | Me | H | 2-Me—, 4-Cl-phenyl | |
| 38 | —CH$_2$O— | Me | H | 2-Me—, 5-Cl-phenyl | |
| 39 | —CH$_2$O— | Me | H | 2-pyridyl | |
| 40 | —CH$_2$O— | Me | H | 3-pyridyl | |
| 41 | —CH$_2$O— | Me | H | 4-pyridyl | |
| 42 | —CH$_2$O— | Me | H | 6-Cl-2-pyridyl | |
| 43 | —CH$_2$O— | Me | H | 6-OCH$_3$-2-pyridyl | |
| 44 | —CH$_2$O— | Me | H | 6-Me-2-pyridyl | |
| 45 | —CH$_2$O— | Me | H | 5-CF$_3$-2-pyridyl | |
| 46 | —CH$_2$O— | Me | H | 2-quinolyl | |
| 47 | —CH$_2$O— | Me | H | 3-Me-2-quinolyl | |
| 48 | —CH$_2$O— | Me | H | 8-Me-2-quinolyl | |
| 49 | —CH$_2$O— | Me | H | 2-pyrimidinyl | |
| 50 | —CH$_2$O— | Me | H | 4-CF$_3$-2-pyrimidinyl | |
| 51 | —CH$_2$O— | Me | H | benzothiazol-2-yl | |
| 52 | —CH$_2$O— | Me | H | 5-Cl-benzothiazol-2-yl | |
| 53 | —CH$_2$O— | Me | H | 6-Cl-benzothiazol-2-yl | |
| 54 | —CH$_2$O— | Me | H | 2-Me-4-methoximinoethyl-1-phenyl | |
| 55 | —CH$_2$O— | Me | H | 2-Me-5-methoximinomethyl-phenyl | |
| 56 | —CH$_2$O— | Me | H | 2,5-Me$_2$-4-methoximinomethyl-phenyl | |
| 57 | —CH$_2$O— | Me | H | 2-Me-4-ethoximinomethyl-phenyl | |
| 58 | —CH$_2$O— | Me | H | 2-Me-5-ethoximinomethyl-phenyl | |
| 59 | —CH$_2$O— | Me | H | 2,5-Me$_2$-4-ethoximinomethyl-phenyl | |
| 60 | —CH$_2$O— | Me | H | 2-Me-4-n-butoximinomethyl-phenyl | |
| 61 | —CH$_2$O— | Me | H | 2,5-Me$_2$-4-n-butoximinomethyl-phenyl | |
| 62 | —CH$_2$O— | Me | H | 2-Me-4-allyloximinomethyl-phenyl | |
| 63 | —CH$_2$O— | Me | H | 2,5-Me$_2$-4-allyloximinomethyl-phenyl | |
| 64 | —CH$_2$O— | Me | H | 1-naphthyl | |
| 65 | —CH$_2$O— | Me | H | 2-naphthyl | |
| 66 | —CH$_2$O— | Me | H | 1-methyl-2-naphthyl | |
| 67 | —CH$_2$O— | Me | H | methyl | |
| 68 | —OCH$_2$— | Me | H | H | |
| 69 | —OCH$_2$— | Me | H | phenyl | |
| 70 | —OCH$_2$— | Me | H | 2-Cl-phenyl | |
| 71 | —O—CH$_2$— | Me | H | 2-Me-phenyl | |
| 72 | —CH$_2$S— | Me | H | Me | |
| 73 | —CH$_2$S— | Me | H | phenyl | |
| 74 | —CH$_2$S— | Me | H | 2-Me-phenyl | |
| 75 | —CH$_2$S— | Me | H | 2,5-Cl$_2$-phenyl | |
| 76 | —CH$_2$S— | Me | H | 2-pyridyl | |
| 77 | —CH$_2$S— | Me | H | 6-Cl-2-pyridyl | |
| 78 | —CH$_2$S— | Me | H | benzothiazol-2-yl | |
| 79 | —CH$_2$S— | Me | H | 5-Cl-benzothiazol-2-yl | |
| 80 | —CH$_2$S— | Me | H | 6-Cl-benzothiazol-2-yl | |
| 81 | —O— | Me | H | phenyl | |
| 82 | —O— | Me | H | 2-naphthyl | |
| 83 | —O— | Me | H | 2-Me-phenyl | |
| 84 | —O— | Me | H | 3-Me-phenyl | |
| 85 | —O— | Me | H | 4-Me-phenyl | |
| 86 | —O— | Me | H | 2-Cl-phenyl | |

TABLE 2-continued

[Structure: phenyl ring with Y-R substituent at ortho position, connected to C(=S)-N(R¹)(R²) with =CH-Me group]

| No. | Y | R¹ | R² | R | Phys. data m. p. [°C.] IR [cm⁻¹] H-NMR [ppm] |
|---|---|---|---|---|---|
| 87 | —O— | Me | H | 3-Cl-phenyl | |
| 88 | —O— | Me | H | 4-Cl-phenyl | |
| 89 | —O— | Me | H | 3-phenoxy-phenyl | |
| 90 | —O— | Me | H | 6-(2-CN-phenoxy)-pyrimidin-4-yl | |
| 91 | —O— | Me | H | 2-pyridyl | |
| 92 | —C≡C— | Me | H | phenyl | |
| 93 | —C≡C— | Me | H | 2-Me-phenyl | |
| 94 | —C≡C— | Me | H | 3-Me-phenyl | |
| 95 | —C≡C— | Me | H | 4-Me-phenyl | |
| 96 | —C≡C— | Me | H | 2-Cl-phenyl | |
| 97 | —C≡C— | Me | H | 2,5-Me₂-phenyl | |
| 98 | —CH₂—O—N=C(Me)— | Me | H | phenyl | |
| 99 | —CH₂—O—N=C(Me)— | Me | H | 2-Me-phenyl | |
| 100 | —CH₂—O—N=C(Me)— | Me | H | 3-Me-phenyl | |
| 101 | —CH₂—O—N=C(Me)— | Me | H | 4-Me-phenyl | |
| 102 | —CH₂—O—N=C(Me)— | Me | H | 2-Cl-phenyl | |
| 103 | —CH₂—O—N=C(Me)— | Me | H | 3-Cl-phenyl | |
| 104 | —CH₂—O—N=C(Me)— | Me | H | 4-Cl-phenyl | |
| 104 | —CH₂—O—N=C(Me)— | Me | H | 2-F-phenyl | |
| 105 | —CH₂—O—N=C(Me)— | Me | H | 3-F-phenyl | |
| 106 | —CH₂—O—N=C(Me)— | Me | H | 4-F-phenyl | |
| 107 | —CH₂—O—N=C(Me)— | Me | H | 2-Br-phenyl | |

TABLE 2-continued

[Structure: phenyl ring with Y-R substituent, connected to C(=S)N(R¹)(R²) and =CH-Me]

| No. | Y | R¹ | R² | R | Phys. data m. p. [°C.] IR [cm⁻¹] H-NMR [ppm] |
|---|---|---|---|---|---|
| 108 | -CH₂-O-N=C(Me)- | Me | H | 3-Br-phenyl | |
| 109 | -CH₂-O-N=C(Me)- | Me | H | 4-Br-phenyl | |
| 110 | -CH₂-O-N=C(Me)- | Me | H | 2-CF₃-phenyl | |
| 111 | -CH₂-O-N=C(Me)- | Me | H | 3-CF₃-phenyl | |
| 112 | -CH₂-O-N=C(Me)- | Me | H | 4-CF₃-phenyl | |
| 113 | -CH₂-O-N=C(Me)- | Me | H | 2-OCH₃-phenyl | |
| 114 | -CH₂-O-N=C(Me)- | Me | H | 3-OCH₃-phenyl | |
| 115 | -CH₂-O-N=C(Me)- | Me | H | 4-OCH₃-phenyl | |
| 116 | -CH₂-O-N=C(Me)- | Me | H | 2-CO₂Me-phenyl | |
| 117 | -CH₂-O-N=C(Me)- | Me | H | 3-CO₂Me-phenyl | |
| 118 | -CH₂-O-N=C(Me)- | Me | H | 4-CO₂Me-phenyl | |
| 119 | -CH₂-O-N=C(Me)- | Me | H | 2,3-Me₂-phenyl | |
| 120 | -CH₂-O-N=C(Me)- | Me | H | 2,4-Me₂-phenyl | |

TABLE 2-continued

| No. | Y | R¹ | R² | R | Phys. data m. p. [°C.] IR [cm⁻¹] H-NMR [ppm] |
|---|---|---|---|---|---|
| 121 | —CH₂—O—N=C(Me) | Me | H | 2,5-Me₂-phenyl | |
| 122 | —CH₂—O—N=C(Me) | Me | H | 2,6-Me₂-phenyl | |
| 123 | —CH₂—O—N=C(Me) | Me | H | 3,4-Me₂-phenyl | |
| 124 | —CH₂—O—N=C(Me) | Me | H | 3,5-Me₂-phenyl | |
| 125 | —CH₂—O—N=C(Me) | Me | H | 2,3-Cl₂-phenyl | |
| 126 | —CH₂—O—N=C(Me) | Me | H | 2,4-Cl₂-phenyl | |
| 127 | —CH₂—O—N=C(Me) | Me | H | 2,5-Cl₂-phenyl | |
| 128 | —CH₂—O—N=C(Me) | Me | H | 2,6-Cl₂-phenyl | |
| 129 | —CH₂—O—N=C(Me) | Me | H | 3,4-Cl₂-phenyl | |
| 130 | —CH₂—O—N=C(Me) | Me | H | 3,5-Cl₂-phenyl | |
| 131 | —CH₂—O—N=C(Me) | Me | H | 2-Cl—, 4-Me-phenyl | |
| 132 | —CH₂—O—N=C(Me) | Me | H | 2-Cl—, 5-Me-phenyl | |
| 133 | —CH₂—O—N=C(Me) | Me | H | 2-Me—, 4-Cl-phenyl | |

TABLE 2-continued

[Structure: phenyl ring with ortho Y-R substituent, attached to C=C(Me) with C(=S)N(R¹)(R²) group]

| No. | Y | R¹ | R² | R | Phys. data m. p. [°C.] IR [cm⁻¹] H-NMR [ppm] |
|-----|---|-----|-----|---|---|
| 134 | —CH₂—O—N=C(Me)— | Me | H | 2-Me—, 5-Cl-phenyl | |
| 135 | —CH₂—O—N=C(Me)— | Me | H | 2-pyridyl | |
| 136 | —CH₂—O—N=C(Me)— | Me | H | 2-naphthyl | |
| 137 | —CH₂—O—N=C(Me)— | Me | H | 1-Me-2-naphthyl | |
| 138 | —CH₂—O—N=C(Me)— | Me | H | 2-furyl | |
| 139 | —CH₂—O— | Me | Me | phenyl | |
| 140 | —CH₂—O— | Et | H | phenyl | |
| 141 | —CH₂—O— | Et | Et | phenyl | |

The novel compounds are suitable as fungicides, insecticides and nematocides.

The active ingredients according to the invention, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Normally, the plants are sprayed or dusted with the active ingredients or the seeds of the plants are treated with the active ingredients.

The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, alumina, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylena octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Examples of such formulations are given below.

I. A solution of 90 parts by weight of compound 2 from Table 1 and 10 parts by weight of N-methyl-α-pyrrolidone, which is suitable for application in the form of very fine drops.

II. A mixture of 20 parts by weight of compound 25 from Table 1, 80 parts by weight of xylene, 10 parts by weight Of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, a dispersion is obtained.

III. An aqueous dispersion of 20 parts by weight of compound 54 from Table 1, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound 130 from Table 1, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

V. A hammer-milled mixture of 80 parts by weight of compound 2 from Table 1, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound 25 from Table 1 and 97 parts by weight of particulate kaolin. The dust contains 3 wt % of the active ingredient.

VII. An intimate mixture of 30 parts by weight of compound 54 from Table 1, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound 130 from Table 1, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound 2 from Table 1, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

The novel compounds are extremely effective on a broad spectrum of phytopathogenic fungi, in particular those from the class consisting of the Ascomycetes and Basidiomycetes. Some of them have systemic mobility and action after application to the soil and foliage.

The fungicidal compounds are of particular interest for controlling a large number of fungi in various crops or their seeds, especially-wheat, rye, barley, oats, rice, Indian corn, lawns, cotton, soybeans, coffee, sugar cane, grapevines, fruit and ornamentals, and in vegetables such as cucumbers, beans and cucurbits.

The compounds are applied by treating the seeds, plants, materials or soil to be protected against fungus attack with a fungicidally effective amount of the active ingredients.

The compounds may be applied before or after infection of the materials, plants or seeds by the fungi.

The compounds I are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia solani in cotton,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The novel compounds may also be used for protecting materials (timber), for example against Paecilomyces variotii.

The fungicidal agents generally contain from 0.1 to 95, and preferably from 0.5 to 90, wt % of active ingredient.

The application rates depend on the type of effect desired, but are generally from 0.02 to 3 kg of active ingredient per hectare.

When the active ingredients are used for treating seed, application rates of from 0.001 to 50, and preferably from 0.01 to 10, g per kg of seed are generally required.

When the agents according to the invention are used as fungicides, they may be employed together with other active ingredients, e.g., herbicides, insecticides, growth regulators, other fungicides and fertilizers.

Use Example 1 Action on Plasmopara viticola

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results of the experiment show that compounds nos. 2, 25 and 54 from Table I, when applied as spray liquors containing 63 ppm of active ingredient, have a very good fungicidal action (0% attack).

Use Example 2 Action on Botrytis cinerea in paprika

Slices of green paprika pods were sprayed to runoff with aqueous formulations containing (dry basis) 80% of active ingredient and 20% of emulsifier. Two hours after the sprayed-on layer had dried, the slices were inoculated with a spore suspension of Botrytis cinerea which contained $1.7 \times 10^6$ spores per ml of a 2% strength biomalt solution. The inoculated slices were then incubated for 4 days in moist chambers. Botrytis spread on the slices was then assessed visually.

The results show that compounds nos. 2, 25 and 54 from Table I, when applied as spray liquors containing 500 ppm of active ingredient, have a very good fungicidal action (5% attack).

We claim:

1. A thioamide of the formula I,

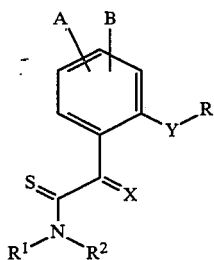

where A and B are identical or different and each is hydrogen,
$C_{1-4}$-alkyl, $C_{1-4}$-alkoxy or halogen;
X is $=N-OCH_3$;
$R^1$ and $R^2$ are hydrogen or $C_{1-4}$-alkyl;
Y is $-CH_2-O-$; and
R is a phenyl with at least one substituent selected from the group consisting of nitro, $C_1-C_4$-alkyl, $C_1-C_4$-alkoxy, $C_1-C_4$-haloalkyl, $C_1-C_4$-alkoximino-$C_1-C_4$-alkyl, aryl, aryloxy, benzyloxy;
with the privoso that at least one substituent is always $C_1-C_4$-alkoximino-$C_1-C_4$-alkyl.

2. The thioamide derivative of claim 1, wherein $R^1$ is hydrogen, $R^2$ is methyl, and A and B are hydrogen.

3. A fungicidal agent containing an inert carrier and a thioamide derivative of the formula I

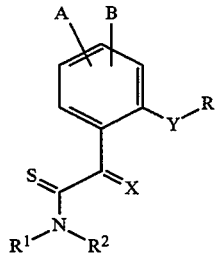

where A and B are identical or different and each is hydrogen,
$C_{1-4}$-alkyl, $C_{1-4}$-alkoxy or halogen;
X is $=N-OCH_3$;
$R^1$ and $R^2$ are hydrogen or $C_{1-4}$-alkyl;
Y is $-CH_2-O-$; and
R is a phenyl with at least one substituent selected from the group consisting of nitro, $C_1-C_4$-alkyl, $C_1-C_4$-alkoxy, $C_1-C_4$-haloalkyl, $C_1-C_4$-alkoximino-$C_1-C_4$-alkyl, aryl, aryloxy, benzyloxy;
with the privoso that at least one substituent is always $C_1-C_4$-alkoximino-$C_1-C_4$-alkyl.

4. A method of combating fungi on plants, comprising treating plants, seeds or soil with a fungicidally effective amount of a compound of the formula I

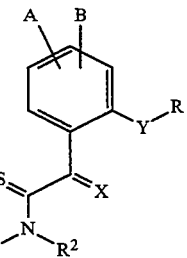

where A and B are identical or different and each is hydrogen,
$C_{1-4}$-alkyl, $C_{1-4}$-alkoxy or halogen;
X is $=N-OCH_3$;
$R^1$ and $R^2$ are hydrogen or $C_{1-4}$-alkyl;
Y is $-CH_2-O-$; and
R is a phenyl with at least one substituent selected from the group consisting of nitro, $C_1-C_4$-alkyl, $C_1-C_4$-alkoxy, $C_1-C_4$-haloalkyl, $C_1-C_4$-alkoximino-$C_1-C_4$-alkyl, aryl, aryloxy, benzyloxy;
with the privoso that at least one substituent is always $C_1-C_4$-alkoximino-$C_1-C_4$-alkyl.

5. A thioamide derivative of the formula I

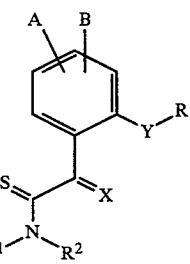

where A and B are hydrogen;
X is $=N-OCH_3$;
$R^1$ is methyl;
$R^2$ is hydrogen;
Y is $-CH_2-O-$; and
R is 4-methoxyiminomethylphenyl.

6. The thioamide of claim 1, wherein R is a phenyl group with a $C_1-C_4$-alkoximino-$C_1-C_4$-alkyl substituent.

7. The thioamide of claim 1, wherein R is a phenyl which is mono- or di-substituted with a methyl group and which has a $C_1-C_4$-alkoximino-$C_1-C_4$-alkyl substituent.

* * * * *